US010127351B2

(12) United States Patent
Chen et al.

(10) Patent No.: US 10,127,351 B2
(45) Date of Patent: Nov. 13, 2018

(54) ACCURATE AND FAST MAPPING OF READS TO GENOME

(71) Applicant: Roche Molecular Systems, Inc., Pleasanton, CA (US)

(72) Inventors: Xiaoying Chen, Alameda, CA (US); Yan Li, Palo Alto, CA (US); Wei-Min Liu, Dublin, CA (US); Xiaoju (Max) Ma, San Carlos, CA (US); Sim-Jasmine Truong, Union City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 332 days.

(21) Appl. No.: 14/954,808

(22) Filed: Nov. 30, 2015

(65) Prior Publication Data

US 2016/0092630 A1 Mar. 31, 2016

Related U.S. Application Data

(63) Continuation of application No. 13/689,314, filed on Nov. 29, 2012, now Pat. No. 9,218,450.

(51) Int. Cl.
*G01N 33/48* (2006.01)
*G06F 19/22* (2011.01)

(52) U.S. Cl.
CPC .................................... *G06F 19/22* (2013.01)

(58) Field of Classification Search
CPC ........................................................ G06F 19/22
USPC .......................................................... 702/19
See application file for complete search history.

(56) References Cited

U.S. PATENT DOCUMENTS

| | | |
|---|---|---|
| 2002/0182630 A1 | 12/2002 | Milosavljevic |
| 2003/0138778 A1 | 7/2003 | Garner et al. |
| 2004/0229269 A1 | 11/2004 | Hashmi et al. |
| 2014/0066317 A1 | 3/2014 | Talasaz |

FOREIGN PATENT DOCUMENTS

| | | |
|---|---|---|
| CN | 1207811 A | 2/1999 |
| CN | 1594564 A | 3/2005 |
| CN | 101019019 A | 8/2007 |

OTHER PUBLICATIONS

Jiang, Tao, et al., "High-performance single-chip exon capture allows accurate whole exome sequencing using the illumina Genome Analyzer," Science China Life Sciences, Oct. 29, 2011, vol. 54, No. 10, pp. 945-952.
Treangen, Todd, J., et al., "Repetitive DNA and next-generation sequencing: computational challenges and solutions," Nature, Jan. 2012 vol. 13, pp. 36-46.
Bhaduri, A., et al., "Rapid identification of non-human sequences in high-throughput sequencing datasets," Bioinformatics, Apr. 2012, vol. 28, No. 8, pp. 1174-1175.
Swaminathan Kankshita, , et al., "Global repeat discovery and estimation of genomic copy number in a large, complex genome using a high-throughput 454 sequence survey," BMC Genomics, May 24, 2007, vol. 8, No. 1, 13 pages.
International Search Report and Written Opinion dated Apr. 3, 2014 in PCT/EP2013/074799, 15 pages.
U.S. Appl. No. 13/689,314, Office Action, dated Apr. 3, 2015.
U.S. Appl. No. 13/689,314, Notice of Allowance, dated Aug. 14, 2015.

*Primary Examiner* — Jerry Lin
(74) *Attorney, Agent, or Firm* — Kilpatrick Townsend and Stockton LLP

(57) ABSTRACT

Accurate and fast mapping of sequencing reads obtained from a targeted sequencing procedure can be provided. Once a target region is selected, alternate regions of the genome that are sufficiently similar to the target region can be identified. If a sequencing read is more similar to the target region than to an alternate region, then the read can be determined as aligning to the target region. The reads aligning to the target region can then be analyzed to determine whether a mutation exists in the target region. Accordingly, a sequencing read can be compared to the target region and the corresponding alternate regions, and not to the entire genome, thereby providing computational efficiency.

21 Claims, 11 Drawing Sheets

Specification includes a Sequence Listing.

```
Query    1       TTTTTTGTAAATCATCTGTCAATCCAAGAGGGGAAAAATATGCAAAGAAGCTATATAA      60
                 ||||||||||||||||||||||||||||||||||||||||||||||||||||||||||||
Sbjct    85431064 TTTTTTGTAAATCATCTGTCAATCCAAGAGGGGAAAAATATGCAAAGAAGCTATATAA    85431123

Query    61      GATATATTTATTTTACAGAGTAACAAGCAATTAGCTAGCAGACAATGAATTAAGGAAAATG   120
                 ||||||||||||||||||||||||||||||||||||||||||||||||||||||||||||
Sbjct    85431124 GATATATTTATTTTACAGAGTAACAAGCAATTAGCTAGCAGACAATGAATTAAGGAAAATG   85431183

Query    121     ACAAAGAACAGCTCAAAGCAATTTCTTACACCAGATCCCTCTCTGAAATCACTGGCACC    180
                 |||||||||||||||||||||||||||||||||||||||||||||||||||||||||| |
Sbjct    85431184 ACAAAGAACAGCTCAAAGCAATTTCTTACAGAGATCCCAGATCCCTCTGAAATCACTGAGCAGG   85431243

Query    181     AGAAAGATTTTCTATGCAC-CACAGAGTAAGTGCTAAAAATGGAGATTCTCTGTTTCTTTT   239
                 ||||||||||||||||||| ||||||||||||||||||||||||||||||||||||||||
Sbjct    85431244 ACAAAGAACAGTTCTATGAATCACAGAGTAAGTGCTAAAAATGGAGATTCTGTGTTTCTTTT   85431303

Query    240     CTTTATTAC   248
                 |||||||||
Sbjct    85431304 CTTTATTAC   85431312
```

FIG. 3

ACAGTTGCACAATATCCTTTTGAAGACCATAACCACCACAGCTAGAACTTATCAAACCC
         G                                                   ─ 520
   531                                        ─ 510

TTTTGTGAAGATCTTGACCAATGGCTAAGTGAAGATGACAATCATGTTGCAGCAATTCAC

TGTAAAGCTGGAAAGGACCAAACTGGTGTAATGATATGCATATTTATTACATCGGGGC
                              A    T A
                            ─ 532 533    ─ 534

AAAT

FIG. 5

| R | Sample | Amplicon | C% | Den | Components | Run |
|---|---|---|---|---|---|---|
| 1 | H089~1600 | CDKN2A_Exon_2.1 | 4.21 | 1069 | 54A>C;99C>A;105C>T;123C>G;129C>T;132C>T | R1_2011_09_22 |
| 2 | H089~800 | CDKN2A_Exon_2.1 | 4.86 | 556 | 54A>C;99C>A;105C>T;123C>G;129C>T;132C>T | R1_2011_09_22 |
| 4 | H089~200 | CDKN2A_Exon_2.1 | 4.84 | 1881 | 54A>C;99C>A;105C>T;123C>G;129C>T;132C>T | R1_2011_09_22 |
| 1 | MEL-188~500 | CDKN2A_Exon_2.1 | 4.88 | 1127 | 54A>C;99C>A;105C>T;123C>G;129C>T;132C>T | R1_2011_11_16 |
| 2 | H089~1000 | CDKN2A_Exon_2.1 | 14.42 | 1762 | 54A>C;99C>A;105C>T;123C>G;129C>T;132C>T | R1_2011_11_16 |
| 2 | H089~200 | CDKN2A_Exon_2.1 | 19.5 | 359 | 54A>C;99C>A;105C>T;123C>G;129C>T;132C>T | R1_2011_11_16 |
| 1 | CRC7~1000 | CDKN2A_Exon_2.1 | 6.56 | 3003 | 54A>C;99C>A;105C>T;123C>G;129C>T;132C>T | R1_2011_11_17 |
| 1 | CRC7~500 | CDKN2A_Exon_2.1 | 3.49 | 1205 | 54A>C;99C>A;105C>T;123C>G;129C>T;132C>T | R1_2011_11_17 |
| 1 | CRC7~200 | CDKN2A_Exon_2.1 | 24.65 | 2665 | 54A>C;99C>A;105C>T;123C>G;129C>T;132C>T | R1_2011_11_17 |
| 1 | CRC7~100 | CDKN2A_Exon_2.1 | 9.11 | 1142 | 54A>C;99C>A;105C>T;123C>G;129C>T;132C>T | R1_2011_11_17 |
| 2 | BR12~1000 | CDKN2A_Exon_2.1 | 7.71 | 3452 | 54A>C;99C>A;105C>T;123C>G;129C>T;132C>T | R1_2011_11_17 |
| 2 | BR12~500 | CDKN2A_Exon_2.1 | 5.21 | 1095 | 54A>C;99C>A;105C>T;123C>G;129C>T;132C>T | R1_2011_11_17 |
| 2 | BR12~200 | CDKN2A_Exon_2.1 | 22.3 | 417 | 54A>C;99C>A;105C>T;123C>G;129C>T;132C>T | R1_2011_11_17 |
| 1 | BR12~200 | CDKN2A_Exon_2.1 | 23.91 | 230 | 54A>C;99C>A;105C>T;123C>G;129C>T;132C>T | R1_2011_12_15 |
| 3 | BR12~200 | CDKN2A_Exon_2.1 | 21.59 | 389 | 54A>C;99C>A;105C>T;123C>G;129C>T;132C>T | R1_2011_12_15 |
| 1 | MEL-188~1000 | CDKN2A_Exon_2.1 | 3.37 | 1631 | 54A>C;99C>A;105C>T;123C>G;129C>T;132C>T | R2_2011_11_03 |
| 1 | MEL-188~500 | CDKN2A_Exon_2.1 | 10.23 | 3030 | 54A>C;99C>A;105C>T;123C>G;129C>T;132C>T | R2_2011_11_03 |
| 1 | MEL-188~100 | CDKN2A_Exon_2.1 | 16.36 | 1094 | 54A>C;99C>A;105C>T;123C>G;129C>T;132C>T | R2_2011_11_03 |
| 2 | H089~1000 | CDKN2A_Exon_2.1 | 13.93 | 2548 | 54A>C;99C>A;105C>T;123C>G;129C>T;132C>T | R2_2011_11_03 |
| 2 | H089~100 | CDKN2A_Exon_2.1 | 12.71 | 1031 | 54A>C;99C>A;105C>T;123C>G;129C>T;132C>T | R2_2011_11_03 |
| 1 | CRC7~1000 | CDKN2A_Exon_2.1 | 3.91 | 2328 | 54A>C;99C>A;105C>T;123C>G;129C>T;132C>T | R2_2011_11_04 |
| 1 | CRC7~500 | CDKN2A_Exon_2.1 | 8.58 | 4485 | 54A>C;99C>A;105C>T;123C>G;129C>T;132C>T | R2_2011_11_04 |

FIG. 9

| | | | | | |
|---|---|---|---|---|---|
| 1 | CRC7~200 | CDKN2A_Exon_2.1 | 9.38 | 2282 | 54A>C;99C>A;105C>T;123C>G;129C>T;132C>T | R2_2011_11_04 |
| 1 | CRC7~100 | CDKN2A_Exon_2.1 | 12.45 | 3028 | 54A>C;99C>A;105C>T;123C>G;129C>T;132C>T | R2_2011_11_04 |
| 2 | BR12~1000 | CDKN2A_Exon_2.1 | 10.25 | 1756 | 54A>C;99C>A;105C>T;123C>G;129C>T;132C>T | R2_2011_11_04 |
| 2 | BR12~500 | CDKN2A_Exon_2.1 | 10.97 | 2398 | 54A>C;99C>A;105C>T;123C>G;129C>T;132C>T | R2_2011_11_04 |
| 2 | BR12~200 | CDKN2A_Exon_2.1 | 9.54 | 1468 | 54A>C;99C>A;105C>T;123C>G;129C>T;132C>T | R2_2011_11_04 |
| 2 | BR12~100 | CDKN2A_Exon_2.1 | 9.04 | 1261 | 54A>C;99C>A;105C>T;123C>G;129C>T;132C>T | R2_2011_11_04 |
| 2 | BR12~500 | CDKN2A_Exon_2.1 | 13.33 | 660 | 54A>C;99C>A;105C>T;123C>G;129C>T;132C>T | R2_2011_12_15 |
| 2 | BR12~200 | CDKN2A_Exon_2.1 | 11.51 | 617 | 54A>C;99C>A;105C>T;123C>G;129C>T;132C>T | R2_2011_12_15 |
| 4 | BR12~500 | CDKN2A_Exon_2.1 | 14.24 | 625 | 54A>C;99C>A;105C>T;123C>G;129C>T;132C>T | R2_2011_12_15 |
| 4 | BR12~200 | CDKN2A_Exon_2.1 | 11.74 | 528 | 54A>C;99C>A;105C>T;123C>G;129C>T;132C>T | R2_2011_12_15 |
| 1 | H089~1600 | PIK3CA_Exon_10 | 6.1 | 3281 | 174A>C;198_199x2:1$GT>C- | R1_2011_09_22 |
| 2 | H089~800 | PIK3CA_Exon_10 | 18.78 | 2215 | 174A>C;198_199x2:1$GT>C- | R1_2011_09_22 |
| 3 | H089~400 | PIK3CA_Exon_10 | 14.37 | 2609 | 174A>C;198_199x2:1$GT>C- | R1_2011_09_22 |
| 1 | MEL-188~1000 | PIK3CA_Exon_10 | 5.41 | 1128 | 174A>C;198_199x2:1$GT>C- | R1_2011_11_16 |
| 1 | MEL-188~500 | PIK3CA_Exon_10 | 23.94 | 1086 | 174A>C;198_199x2:1$GT>C- | R1_2011_11_16 |
| 2 | H089~1000 | PIK3CA_Exon_10 | 11.35 | 2052 | 174A>C;198_199x2:1$GT>C- | R1_2011_11_16 |
| 2 | H089~500 | PIK3CA_Exon_10 | 15.02 | 1558 | 174A>C;198_199x2:1$GT>C- | R1_2011_11_16 |
| 2 | H089~200 | PIK3CA_Exon_10 | 15.99 | 369 | 174A>C;198_199x2:1$GT>C- | R1_2011_11_16 |
| 2 | H089~100 | PIK3CA_Exon_10 | 16.25 | 277 | 174A>C;198_199x2:1$GT>C- | R1_2011_11_16 |
| 1 | CRC7~1000 | PIK3CA_Exon_10 | 17.86 | 1624 | 174A>C;198_199x2:1$GT>C- | R1_2011_11_17 |
| 1 | CRC7~500 | PIK3CA_Exon_10 | 25.55 | 1397 | 174A>C;198_199x2:1$GT>C- | R1_2011_11_17 |
| 1 | CRC7~200 | PIK3CA_Exon_10 | 25.15 | 978 | 174A>C;198_199x2:1$GT>C- | R1_2011_11_17 |
| 1 | CRC7~100 | PIK3CA_Exon_10 | 37.46 | 678 | 174A>C;198_199x2:1$GT>C- | R1_2011_11_17 |
| 2 | BR12~1000 | PIK3CA_Exon_10 | 10.85 | 2701 | 174A>C;198_199x2:1$GT>C- | R1_2011_11_17 |
| 2 | BR12~500 | PIK3CA_Exon_10 | 18.38 | 1997 | 174A>C;198_199x2:1$GT>C- | R1_2011_11_17 |
| 2 | BR12~200 | PIK3CA_Exon_10 | 29.49 | 390 | 174A>C;198_199x2:1$GT>C- | R1_2011_11_17 |
| 2 | BR12~100 | PIK3CA_Exon_10 | 31.43 | 105 | 174A>C;198_199x2:1$GT>C- | R1_2011_11_17 |
| 1 | BR12~500 | PIK3CA_Exon_10 | 17.54 | 690 | 174A>C;198_199x2:1$GT>C- | R1_2011_12_15 |
| 1 | BR12~200 | PIK3CA_Exon_10 | 23.11 | 411 | 174A>C;198_199x2:1$GT>C- | R1_2011_12_15 |
| 3 | BR12~500 | PIK3CA_Exon_10 | 20.51 | 1024 | 174A>C;198_199x2:1$GT>C- | R1_2011_12_15 |
| 3 | BR12~200 | PIK3CA_Exon_10 | 23.79 | 517 | 174A>C;198_199x2:1$GT>C- | R1_2011_12_15 |
| 1 | MEL-188~1000 | PIK3CA_Exon_10 | 27.91 | 86 | 174A>C;198_199x2:1$GT>C- | R2_2011_11_03 |
| 1 | MEL-188~500 | PIK3CA_Exon_10 | 28 | 75 | 174A>C;198_199x2:1$GT>C- | R2_2011_11_03 |
| 2 | H089~1000 | PIK3CA_Exon_10 | 18.8 | 367 | 174A>C;198_199x2:1$GT>C- | R2_2011_11_03 |
| 2 | H089~500 | PIK3CA_Exon_10 | 13.46 | 327 | 174A>C;198_199x2:1$GT>C- | R2_2011_11_03 |
| 2 | H089~200 | PIK3CA_Exon_10 | 30.18 | 222 | 174A>C;198_199x2:1$GT>C- | R2_2011_11_03 |
| 1 | CRC7~1000 | PIK3CA_Exon_10 | 20.83 | 144 | 174A>C;198_199x2:1$GT>C- | R2_2011_11_04 |
| 1 | CRC7~500 | PIK3CA_Exon_10 | 19.05 | 189 | 174A>C;198_199x2:1$GT>C- | R2_2011_11_04 |
| 1 | CRC7~200 | PIK3CA_Exon_10 | 35.22 | 159 | 174A>C;198_199x2:1$GT>C- | R2_2011_11_04 |
| 1 | CRC7~100 | PIK3CA_Exon_10 | 30.59 | 85 | 174A>C;198_199x2:1$GT>C- | R2_2011_11_04 |
| 2 | BR12~1000 | PIK3CA_Exon_10 | 21.97 | 223 | 174A>C;198_199x2:1$GT>C | R2_2011_11_04 |
| 2 | BR12~500 | PIK3CA_Exon_10 | 18.92 | 259 | 174A>C;198_199x2:1$GT>C- | R2_2011_11_04 |
| 2 | BR12~200 | PIK3CA_Exon_10 | 16 | 225 | 174A>C;198_199x2:1$GT>C- | R2_2011_11_04 |

FIG. 9 (Cont.)

| 2 | BR12~500 | PIK3CA_Exon_10 | 15.28 | 144 | 174A>C;198_199x2:1$GT>C- | R2_2011_12_15 |
|---|---|---|---|---|---|---|
| 2 | BR12~200 | PIK3CA_Exon_10 | 21.57 | 204 | 174A>C;198_199x2:1$GT>C- | R2_2011_12_15 |
| 4 | BR12~200 | PIK3CA_Exon_10 | 23.6 | 163 | 174A>C;198_199x2:1$GT>C- | R2_2011_12_15 |
| 3 | H089~400 | PTEN_Exon_5.1.2 | 4.26 | 1362 | 147G>A;155A>T;157G>A | R1_2011_09_22 |
| 4 | H089~200 | PTEN_Exon_5.1.2 | 11.16 | 457 | 147G>A;155A>T;157G>A | R1_2011_09_22 |
| 1 | MEL-188~500 | PTEN_Exon_5.1.2 | 1.77 | 2314 | 147G>A;155A>T;157G>A | R1_2011_11_16 |
| 2 | H089~1000 | PTEN_Exon_5.1.2 | 7.32 | 1748 | 147G>A;155A>T;157G>A | R1_2011_11_16 |
| 2 | H089~500 | PTEN_Exon_5.1.2 | 6.3 | 1048 | 147G>A;155A>T;157G>A | R1_2011_11_16 |
| 2 | H089~200 | PTEN_Exon_5.1.2 | 11.19 | 429 | 147G>A;155A>T;157G>A | R1_2011_11_16 |
| 1 | CRC7~1000 | PTEN_Exon_5.1.2 | 2.13 | 1222 | 147G>A;155A>T;157G>A | R1_2011_11_17 |
| 1 | CRC7~500 | PTEN_Exon_5.1.2 | 3.29 | 1064 | 147G>A;155A>T;157G>A | R1_2011_11_17 |
| 1 | CRC7~200 | PTEN_Exon_5.1.2 | 6.35 | 1023 | 147G>A;155A>T;157G>A | R1_2011_11_17 |
| 1 | CRC7~100 | PTEN_Exon_5.1.2 | 8.66 | 381 | 147G>A;155A>T;157G>A | R1_2011_11_17 |
| 2 | BR12~1000 | PTEN_Exon_5.1.2 | 2.05 | 1850 | 147G>A;155A>T;157G>A | R1_2011_11_17 |
| 2 | BR12~500 | PTEN_Exon_5.1.2 | 5.67 | 934 | 147G>A;155A>T;157G>A | R1_2011_11_17 |
| 1 | MEL-188~1000 | PTEN_Exon_5.1.2 | 1.55 | 1222 | 147G>A;155A>T;157G>A | R2_2011_11_03 |
| 1 | MEL-188~500 | PTEN_Exon_5.1.2 | 1.07 | 1595 | 147G>A;155A>T;157G>A | R2_2011_11_03 |
| 1 | MEL-188~200 | PTEN_Exon_5.1.2 | 2.36 | 975 | 147G>A;155A>T;157G>A | R2_2011_11_03 |
| 1 | MEL-188~100 | PTEN_Exon_5.1.2 | 8.71 | 402 | 147G>A;155A>T;157G>A | R2_2011_11_03 |
| 2 | H089~1000 | PTEN_Exon_5.1.2 | 12.1 | 1322 | 147G>A;155A>T;157G>A | R2_2011_11_03 |
| 2 | H089~500 | PTEN_Exon_5.1.2 | 5.93 | 1232 | 147G>A;155A>T;157G>A | R2_2011_11_03 |
| 2 | H089~200 | PTEN_Exon_5.1.2 | 9.44 | 752 | 147G>A;155A>T;157G>A | R2_2011_11_03 |
| 2 | H089~100 | PTEN_Exon_5.1.2 | 12.53 | 391 | 147G>A;155A>T;157G>A | R2_2011_11_03 |
| 1 | CRC7~1000 | PTEN_Exon_5.1.2 | 3.51 | 542 | 147G>A;155A>T;157G>A | R2_2011_11_04 |
| 1 | CRC7~500 | PTEN_Exon_5.1.2 | 5.25 | 1104 | 147G>A;155A>T;157G>A | R2_2011_11_04 |
| 1 | CRC7~200 | PTEN_Exon_5.1.2 | 4.17 | 539 | 147G>A;155A>T;157G>A | R2_2011_11_04 |
| 1 | CRC7~100 | PTEN_Exon_5.1.2 | 7.83 | 766 | 147G>A;155A>T;157G>A | R2_2011_11_04 |
| 2 | BR12~500 | PTEN_Exon_5.1.2 | 5.82 | 825 | 147G>A;155A>T;157G>A | R2_2011_11_04 |
| 2 | BR12~100 | PTEN_Exon_5.1.2 | 6.67 | 450 | 147G>A;155A>T;157G>A | R2_2011_11_04 |

FIG. 9 (Cont.)

SEQUENCE LISTING

<160> NUMBER OF SEQ ID NOS: 12

<210> SEQ ID NO 1
<211> LENGTH: 206
<212> TYPE: DNA

<213> ORGANISM: Artificial Sequence
<220> FEATURE:
<223> OTHER INFORMATION: synthetic reference sequence 200 target region of the genome

<400> SEQUENCE: 1

```
gggagagcag gcagcgggcg gcggggagca gcatggagcc ggcggcgggg agcagcatgg      60
agccttcggc tgactggctg gccacggccg cggcccgggg tcgggtagag gaggtgcggg     120
cgctgctgga ggcggggggcg ctgcccaacg caccgaatag ttacggtcgg aggccgatcc    180
aggtgggtag agggtctgca gcggga                                          206
```

<210> SEQ ID NO 2
<211> LENGTH: 242
<212> TYPE: DNA
<213> ORGANISM: Artificial Sequence
<220> FEATURE:
<223> OTHER INFORMATION: synthetic filtered sequence read 250

<400> SEQUENCE: 2

```
gggagagcag gcagctgagg tggagtacag agcccaccag ccccgccgtc cgggagcgct      60
gcgcttctcc gaggcctgat gagtatggac gctgctttgg cttttgggtta ggagaagggc    120
actgggagca cgcagtaggt gctcgagtgg ctgagtggca ctgggctgag gagaacacac    180
agagccaggt ccagtcttct ggaggcagga ggtgggcgcc agggacgggg tctgcagcgg    240
ga                                                                   242
```

<210> SEQ ID NO 3
<211> LENGTH: 248
<212> TYPE: DNA
<213> ORGANISM: Artificial Sequence
<220> FEATURE:
<223> OTHER INFORMATION: synthetic sequence read 310

<400> SEQUENCE: 3

```
tttttttgta aatcatctgt gaatccagag gggaaaaata tgacaaagaa agctatataa      60
gatattattt tattttacag agtaacagac tagctagaga caatgaatta agggaaaatg    120
acaaagaaca gctcaaagca atttctacac gagatcctct ctctgaaatc actgcgcagg    180
agaaagattt tctatggacc acaggtaagt gctaaaatgg agattctctg tttcttttc    240
tttattac                                                             248
```

<210> SEQ ID NO 4
<211> LENGTH: 249
<212> TYPE: DNA
<213> ORGANISM: Artificial Sequence
<220> FEATURE:
<223> OTHER INFORMATION: synthetic target sequence 320, target region

<400> SEQUENCE: 4

```
tttttctgta aatcatctgt gaatccagag gggaaaaata tgacaaagaa agctatataa      60
gatattattt tattttacag agtaacagac tagctagaga caatgaatta agggaaaatg    120
acaaagaaca gctcaaagca atttctacac gagatcctct ctctgaaatc actgagcagg    180
agaaagattt tctatggagt cacaggtaag tgctaaaatg gagattctct gtttcttttt    240
ctttattac                                                            249
```

<210> SEQ ID NO 5
<211> LENGTH: 217
<212> TYPE: DNA

<213> ORGANISM: Artificial Sequence
<220> FEATURE:
<223> OTHER INFORMATION: synthetic target sequence 420, target region

<400> SEQUENCE: 5

```
ctggctctga ccattctgtt ctctctggca ggtcatgatg atgggcagcg cccgagtggc    60
ggagctgctg ctgctccacg gcgcggagcc caactgcgcc gaccccgcca ctctcacccg   120
acccgtgcac gacgctgccc gggagggctt cctggacacg ctggtggtgc tgcaccgggc   180
cggggcgcgg ctggacgtgc gcgatgcctg gggccgt                            217
```

<210> SEQ ID NO 6
<211> LENGTH: 217
<212> TYPE: DNA
<213> ORGANISM: Artificial Sequence
<220> FEATURE:
<223> OTHER INFORMATION: synthetic sequence read 410

<400> SEQUENCE: 6

```
ctggctctga ccactctgct ctctctggca ggtcatgatg atgggcagcg cccgcgtggc    60
ggagctgctg ctgctccacg gcgcggagcc caactgcgca gaccctgcca ctctcacccg   120
accggtgcat gatgctgccc gggagggctt cctggacacg ctggtggtgc tgcaccgggc   180
cggggcgcgg ctggacgtgc gcgatgcctg gggtcgt                            217
```

<210> SEQ ID NO 7
<211> LENGTH: 184
<212> TYPE: DNA
<213> ORGANISM: Artificial Sequence
<220> FEATURE:
<223> OTHER INFORMATION: synthetic target sequence 520, target region

<400> SEQUENCE: 7

```
acagttgcac aatatccttt tgaagaccat aacccaccac agctagaact tatcaaaccc    60
ttttgtgaag atcttgacca atggctaagt gaagatgaca atcatgttgc agcaattcac   120
tgtaaagctg gaaagggacg aactggtgta atgatatgtg catatttatt acatcggggc   180
aaat                                                                184
```

<210> SEQ ID NO 8
<211> LENGTH: 184
<212> TYPE: DNA
<213> ORGANISM: Artificial Sequence
<220> FEATURE:
<223> OTHER INFORMATION: synthetic sequence read 510

<400> SEQUENCE: 8

```
acagttgcgc aatatccttt tgaagaccat aacccaccac agctagaact tatcaaaccc    60
ttttgtgaag atcttgacca atggctaagt gaagatgaca atcatgttgc agcaattcac   120
tgtaaagctg gaaagggacg aactggtata atgatttatg catatttatt acatcggggc   180
aaat                                                                184
```

<210> SEQ ID NO 9
<211> LENGTH: 14
<212> TYPE: DNA
<213> ORGANISM: Artificial Sequence
<220> FEATURE:
<223> OTHER INFORMATION: synthetic EGFR exon 19 positions 2237-2248

<400> SEQUENCE: 9

```
aattaagaga agcc                                                      14
```

```
<210> SEQ ID NO 10
<211> LENGTH: 14
<212> TYPE: DNA
<213> ORGANISM: Artificial Sequence
<220> FEATURE:
<223> OTHER INFORMATION: synthetic mutant EGFR exon 19 positions
      2237-2248

<400> SEQUENCE: 10
aattaagaga accc                                                          14

<210> SEQ ID NO 11
<211> LENGTH: 18
<212> TYPE: DNA
<213> ORGANISM: Artificial Sequence
<220> FEATURE:
<223> OTHER INFORMATION: synthetic EGFR exon 19 positions 2237-2250

<400> SEQUENCE: 11
aattaagaga agcacccg                                                      18

<210> SEQ ID NO 12
<211> LENGTH: 18
<212> TYPE: DNA
<213> ORGANISM: Artificial Sequence
<220> FEATURE:
<223> OTHER INFORMATION: synthetic mutant EGFR exon 19 positions
      2237-2250

<400> SEQUENCE: 12
aattaagaga agccccccg                                                     18
```

ACCURATE AND FAST MAPPING OF READS TO GENOME

CROSS-REFERENCES TO RELATED APPLICATIONS

This patent application is a continuation of U.S. patent application Ser. No. 13/689,314, filed Nov. 29, 2012, entitled "Accurate and Fast Mapping of Reads to Genome," the content of which is incorporated herein by reference in its entirety for all purposes.

FIELD OF THE INVENTION

The present disclosure generally relates to the analysis of a biological sample using genomic sequencing, and more particularly to accurate and fast mapping of sequencing reads obtained from a targeted sequencing process.

BACKGROUND

For a particular patient, a doctor may want to analyze one or more particular (target) regions of the patient's genome (e.g., 100-500 bases per region). For example, a specific part of a gene of a patient may be tested for mutations. As only certain regions are to be analyzed, techniques have been developed for increasing the percentage of genomic segments (e.g., DNA fragments) in a sample that are from the target region(s). Such techniques include amplification and enrichment of a target region.

In amplification, primers that hybridize to a target region are used to amplify genomic segments that have sequences that correspond to the target region. The desired result is that the sample would contain many genomic segments of the target region, and thus when the genomic segments are sequenced, a high percentage of the reads would correspond to the target region. Thus, significant sequencing effort is not wasted in sequencing genomic segments from non-target regions of the genome. In enrichment, probes that hybridize to a target region can be used to capture genomic segments that correspond to the target region, thereby increasing the percentage of reads that correspond to the target region.

However, in both amplification and enrichment, genomic segments from other parts of the genome are still read. As a consequence, current techniques align (map) the reads to the entire genome to ensure accuracy, particularly when a target region is being analyzed for mutations relative to a reference genome. That is, once a sequence read is obtained, the sequence is compared to the reference genome to find the genomic location that is a best match to the read. After the reads have been aligned, the reads that aligned to a target region are then analyzed. This alignment to the entire genome is computationally expensive.

It is therefore desirable to provide improved methods, systems, and apparatuses that are more computationally efficient.

BRIEF SUMMARY

Embodiments can provide an accurate and fast mapping of sequencing reads obtained from a targeted sequencing. For example, once a target region is selected, alternate regions of the genome that are sufficiently similar to the target region can be identified. If a sequencing read is more similar to the target region than to an alternate region, then the read can be determined as aligning to the target region. The reads aligning to the target region can then be analyzed to determine whether a mutation exists in the target region. Accordingly, a sequencing read can then be compared to the target region and the corresponding alternate regions, and not to the entire genome, thereby providing computational efficiency.

According to one embodiment, a method detects variants in a target region of a sample genome of an organism. A plurality of sequence reads are received. The sequence reads are obtained from sequencing genomic segments in a sample obtained from the organism, where the sequencing includes targeting genomic segments from the target region. One or more alternate regions that have a respective first number of variations from the target region of a reference genome are identified. Each respective first number is greater than one and less than a first threshold number. A computer system performs an alignment of the plurality of sequence reads to the target region of the reference genome to identify a set of sequence reads that align to the target region of the reference genome with less than a second threshold number of variations. Sequence reads that align to one of the alternate regions with a second number of variations that is less than a third threshold number can be removed from the set. The remaining sequence reads of the set are analyzed to determine variants in the target region of the sample genome.

Other embodiments are directed to systems, apparatuses, and computer readable media associated with methods described herein.

A better understanding of the nature and advantages of the present invention may be gained with reference to the following detailed description and the accompanying drawings.

Definitions

As used herein, a "biological sample" includes nucleic acid molecules that are from the genome of the organism from which the sample was obtained. For example, the sample can include cells that contain a genome encoded in chromosomes. A "genomic segment" is a nucleic acid molecule that is wholly or partially sequenced, where the molecule is from the genome of an organism. The segment can be created by fragmenting larger pieces of a genome, e.g., by subjecting a cell to sonic waves. A genomic segment can be sequenced to provide a "sequencing read" (also called a "sequence read" or just a "read"). The sequencing read may be of the entire genomic segment or just part of the segment.

A "target region" is a region of the genome where the fragments have been amplified using primers and an amplification process or have been enriched using probes. An "alternate region" is a region that is similar to a target region, e.g., by having a less than a specified number of variations, which may be specified as a percentage of the total bases of a sequence. A "reference genome" (also simply called "reference") is any known sequence to which sequence reads are aligned. The reference genome may correspond to all or only part of the genome for an organism. A reference genome can also include genomes of more than one organism. For example, a sequence read could also be compared against a database of viruses, as such viruses could be in the biological sample.

A variation (also called a variant or mutation) refers to a difference between two sequences. For example, a difference between a sequence read and a target region of a reference genome can get counted, and a mutation might be identified (e.g., if enough sequence read show the mutation). A variation can, for example, be a change of one base to one or more other bases, an insertion of one or more bases, or a deletion of one or more bases. A variation can occur in one or both chromosomes. Embodiments can be used to determine whether a sequence read is evidence of a mutation or actually a genomic segment from a similar part of the genome.

BRIEF DESCRIPTION OF THE DRAWINGS

FIG. 2A shows the reference sequence (SEQ ID NO:1) for a target region of the genome. FIG. 2B shows a sequence read (SEQ ID NO:2) that was filtered out by MCF according to embodiments of the present invention.

FIG. 3 shows a comparison of a sequence read 310 (SEQ ID NO:3) relative to a target sequence (i.e. target region) 320 (SEQ ID NO:4) according to embodiments of the present invention.

FIG. 5 shows another example of a comparison of a sequence read 510 (SEQ ID NO:8) relative to a target sequence (i.e. target region) 520 (SEQ ID NO:7) according to embodiments of the present invention.

FIG. 9 is a table showing complex mutations that appear in multiple samples and multiple runs according to embodiments of the present invention.

DETAILED DESCRIPTION

Figure 1:
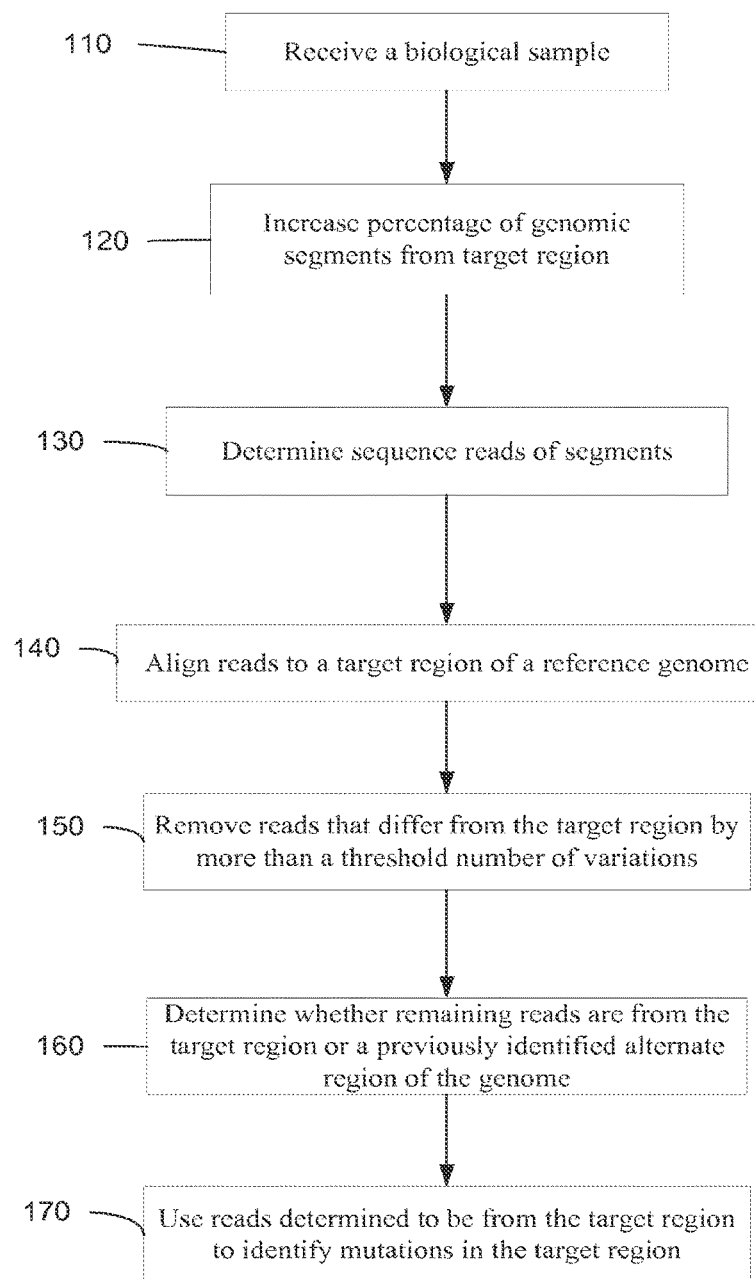
FIG. 1 is a flowchart illustrating a method 100 of detecting variants in a target region of a sample genome of an organism.

A specific region of a genome can be analyzed efficiently using targeted sequencing. For example, the percentage of genomic segments of a biological sample can be increased by cloning segments that correspond to a target region (e.g., using primers in an amplification process, such as polymerase chain reaction (PCR)) and/or using probes to preferentially capture segments that correspond to a target region. The genomic segments in the target-increased sample (an example of a biological sample) can be sequenced and analyzed to investigate possible mutations in a target region.

As one is only interested in the target regions, one could align the sequence reads only to the target region(s). This would reduce the computational effort relative to aligning the reads to the entire reference genome. However, such a process can lead to errors. For example, in variant detection using high throughput next generation sequencing with a prior step of amplification or enrichment, it is possible that the amplicon/enriched library (target-increased sample) contains false positive reads, i.e., the reads corresponding to genomic segments that do not correspond the intended target region(s). These reads can lead to incorrect mutation report and can provide misleading information for product development or even wrong diagnostic conclusions. The false positives can be reduced by various methods, such as proper design of the primers and development of high fidelity enzymes. However, false positives still remain.

Embodiments can provide solutions to exclude the false positive reads in an efficient manner. As an example, for the reads that are significantly different from the target, a mutation count filter (MCF) to identify and exclude the reads that are significantly different from a target. Another example is to identify false positive reads that correspond to alternate regions that are similar to a target region.

In one embodiment, the alternate (non-target) regions of the genome are specifically identified. The variations between the alternate regions and the target region can be specifically noted. When a sequence read matches the target region except for the certain number of specific variations characteristic of an identified alternate region, that sequence read can be discarded from the analysis of the target region. In this manner, the sequence reads only need to be aligned to the target region, and false positives are discarded.

The alternate regions can be identified ahead of time and stored in a database. Once a target region is selected, the alternate regions can be read out. In an implementation that determines the identified regions, a report of complex mutations (e.g., more than one variation relative to the target region) can be used to find variant combinations that appear in multiple runs and/or multiple samples. If the sequence of the complex mutation is common (i.e. detected a sufficient amount of times), the complex mutation sequence can be aligned to the reference genome to identify if it corresponds to an alternate region. Thus, reads that correspond to the specific variant combination (i.e. the variant combination given by the alternate relative to the target region) can be discarded from the analysis for mutations of the target region.

In some embodiments, multiple target regions can be analyzed at the same time. In such embodiments, sequencing reads can be compared to all of the target regions and corresponding alternate regions. But, since the number of regions is relatively small compared to the entire reference genome, the alignment is still efficient. For example, embodiments have been successfully used on data of the Cancer Gene Panel project with up to 60 amplicons of 12 genes related to cancer.

I. Targeted Sequencing

A sequencing run may generate multiple millions of reads. It is very challenging to map all reads to the whole genome in terms of computational time and memory resource. For target-increased runs (e.g., with amplification or enrichment), the major interest is in the reads that map to the target regions (e.g., a particular region of a gene or the whole gene). However, if the computer system only maps to the reference at these target regions, it may overestimate the coverage of reads at the target regions by missing that some reads may be better mapped to other parts of the genome. But, mapping to the entire genome is expensive. Accordingly, embodiments can map to only certain parts of the genome while provide accurate results.

FIG. 1 is a flowchart illustrating a method 100 of detecting variants in a target region of a sample genome of an organism. As with other methods, embodiments can include all or some of the steps described, and some steps may be performed with a computer system. The results of method 100 may be used by a doctor in determining a diagnosis of the organism.

At block 110, a biological sample is received. The biological sample includes DNA, which may be in genomic segments of chromosomes or as intact chromosomes. For example, some cells may be obtained from a patient who is being tested for mutations in particular regions of the genome. The cells could be obtained from a biopsy of a tumor that is being tested for cancer.

The DNA of the sample can be fragmented, e.g., by sonication or other suitable methods to obtain smaller genomic segments. For example, genomic segments of 200-500 bases long can be obtained. For certain sequencing procedures, genomic segments of about this length are preferred. However, embodiments can use genomic segments of any length.

The genomic segments can be marked with a barcode or multiplex identifier (MID). For example, a sequence of 10 bases can be added (e.g., using a ligase) to the end of a genomic segment. In this manner, segments from various samples can be sequenced in parallel during a same sequencing run using the ID to multiplex. The ID can be read as part of a sequence read, and reads with the same ID can be attributed to a same sample and analyzed as a group. The different samples can be from different people or the same person (e.g., different biopsies), and may use different experimental conditions At block 120, the percentage of genomic segments from target region in the sample is increased. In various embodiments, the percentage can be increased by amplifying and/or enriching the sample for DNA from one or more targeted regions of the genome. The resulting sample can be referred to as a target-increased sample. Typically, a target region would have diagnostic relevance, e.g., to see if there is any cancer-related mutation.

As examples, the target region can be about a few hundred bases, e.g., 150-250 bases, 150-400 bases, or 200-600 bases. The addition of a sample-specific ID can occur at different points. For example, the ID could be added after the amplification/enrichment and then the samples mixed together. In this way, the different samples could be amplified or enriched for different target regions. In one implementation, about 60 target regions are used.

In one embodiment, forward and reverse primers can be used to amplify a target region. These forward and reverse primers can be of various length, e.g., about 15-30 bases long. Ideally, the primers only amplify one part of the genome. However, with a length of about 15 bases, this is not always possible. Even using 30 bases may not always provide unique amplification. Longer primers could be used, but longer primers may not hybridize efficiently.

In another embodiment, probes can be used to capture genomic segments that correspond to the target region. For example, probes that are designed to hybridize to the target region can be placed on a surface. Then, the genomic segments can be placed over the surface and the segments of the target region will preferentially be hybridized. For example, a microarray with the probes can be constructed, and the segments washed over the microarray. The specificity of the probes can suffer from the same problems as the primer for amplification. Some probes can be 70 bases long for a target region of 300 bases long. As the probe can capture either end of a genomic segment, the segments could, for example, span a region of 300 bases to about 550 bases for genomic segments of up to 250 bases. In another embodiment, both amplification and enrichment could be performed.

Although some other areas of the genome may also be amplified if the primers are not specific enough and some other areas of the genome might hybridize to the enrichment probes, the percentage of segments from the target regions should increase. Due to imperfect specificity in primer design, the biochemistry of an experiment could cause other regions to be amplified.

At block 130, sequence reads are determined from genomic segments in the sample. In the sequencing process, the clones of a same segment created in an amplification process can have its sequence determined separately (and counted later). In some implementations, about 3,000 reads per sample are obtained. The number of reads can depend on the size of the sample, how much amplification was performed as part of the target increase, and the bandwidth of the sequencing process (i.e., how much sequencing the apparatus is set for, e.g., how many beads are used). Thus, not all of the segments in a sample might be sequenced. In one embodiment, the reads are about 150-250 bases long. One skilled in the art will appreciate the varied techniques available for performing the sequencing.

The sequencing process can be performed by various techniques. In one embodiment, the fragments can undergo an amplification as part of the sequencing. Where amplification was used to create a target-increased sample, this amplification would be a second amplification step. The second amplification can provide a stronger signal (e.g., a fluorescent signal corresponding to a particular base: A, C, G, or T) than if the second amplification was not performed. And, the different amplicons do not result in separate sequence reads.

In one example of a sequencing process, amplified fragments from step 120 (e.g., where amplification occurred in a solution) can each be attached to a bead. The attached fragment can then be amplified on the bead, and one sequence read can be obtained from each bead. For embodiments that use a surface, a fragment can be attached to a surface and then amplified to create a single cluster on the surface. A single sequence read can be obtained for each cluster. A sequence read can be for an entire length of a genomic segment, part of one end, or part of both ends.

A sequence read can include the bases correspond to the actual segment, the bases corresponding to a sample-specific ID, and special tags (e.g., 25 bases long) that may be used as part of the sequencing. The special tags can include part of an adapter that is ligated to the end of a fragment for receiving a universal primer, and part of the adapter could be read during the sequencing.

In one aspect, the sequencing can be performed on any genomic segment in the enriched sample, even if the segment is not a target. Some of these genomic segments may correspond to segments that were originally in the sample, but which were not targets. Some of the non-target segments that are sequenced can also be attributed to amplification or capturing of unintended parts of the genome.

At block 140, a plurality of the sequence reads are aligned to a target region of a reference genome. By aligning, the process can compare the sequence reads to the target region to determine the number of variations between the sequence read and the target region. A perfect match would show no variations. A portion or all of the sequence reads obtained may be used in the alignment process. For example, if the length of a read is too short or too long, then it may be removed before alignment.

The alignment can be made so as to minimize the number of variations between the sequence read and the target region. Note that the sequence read may be smaller than the target region or larger. If the sequence read is larger, the number of variations could be counted only in the target region.

In an embodiment, the reads are only aligned to a target region, thereby saving computational effort. As the alignment can be specific to only the one or more target region(s), the alignment can be fast as the entire genome does not have to be searched. Also, as the percentage of segments corresponding to a target region is increased, a substantial number of the reads should match favorably to the target region (e.g., relatively few variations).

In one embodiment, if multiple target regions are used, then a sequence read can be compared to all of the target regions, and the target region that provides the best alignment can be identified. For example, the different target regions can be different genes or different exons with a gene. Thus, the exon with the best alignment could be identified.

If a barcode or ID is used, it can be removed before aligning. The ID can be used to organize all of the reads for a particular sample into one group. In this manner, mutations from other samples will not impact the analysis of the present sample. This grouping is referred to as demultiplexing. Each sample could be aligned to a different reference genome or different part of the reference genome. As different samples may have different target regions, the ID can be used to determine which target region(s) of a reference genome should be compared for the alignment.

In step 150, sequence reads that differ from a target region by more than a threshold number of variations are discarded from analysis for the target region. If the number of variations is more than the threshold, this is an indication that the genomic segment corresponding to the sequence read did not come from the target region, given that the read was so different. However, there would be allowance for some variations, as later analysis may attempt to identify mutations, which otherwise would be missed.

Example values for the threshold are 5-10 bases. In one embodiment, the threshold is dependent on the size of the target region. For example, if the target region is 200 bases, then the number of variations can be capped at 20, or 10%. If the target regions was 150 bases, then the threshold could be 15 bases.

For each target region, the reads that have less than (and potentially equal to) the threshold can be identified, e.g., as a group. This group of read can then be analyzed further in relation to the target region. In some embodiments, if a read satisfies the threshold for more than one target region, then it can be added to both groups. Such a read can be tracked such that it is not ultimately counted as a mutation for more than one target region.

At block 160, it is determined whether the remaining sequence reads are from the target region or from a previously identified alternate region of the genome. For example, the number of variations between the read and the target region, and the number of variations between the read and the alternate region may be used to determine which is a better match. The number of variations between the read and an alternate region can be determined by aligning the read to the alternate region directly or by using the known variations between the target region and the alternate region. In either case, as the alternate regions are already identified, the amount of additional work is relatively small compared to an alignment to the whole genome.

The alternate regions can be identified as regions that are similar to the target region, e.g., the number of variations is within a threshold. Such a threshold can be less than the threshold used in block 150. Example techniques for identifying alternate regions is described in more detail below.

In addition to determining whether the remaining sequence reads are from the target region or from an alternate region of the genome, one can also determine if the mutation is a common mutation by comparing to known databases of common mutations. These mutations can be for the same target region. Such common mutations might occur for a certain population or subpopulation of people, which is different than the reference genome used. Also, the alternate regions could be from a different genome, e.g., from a genomic database of viruses that might end up in the biological sample.

At block 170, sequence reads from the target region are used to identify mutations in the target region. As part of this step, the frequency of each variations can be determined. For example, for a particular position in a target region, the number of times a G mutation appears instead of a normal A can be counted. A percentage of times the G mutations is seen can be determined from the total reads that aligned to that position. In one embodiment, the percentage for a particular mutation can be required to be greater than a threshold (abundance filter) to be considered an actual mutation. Variations that occur together can be identified, and may be categorized as part of a same mutation.

A doctor could look at the identified mutations and use it to diagnose a predisposition to cancer or to identify a tumor as having cancer. For example, the mutations may be similar to mutations for different regions that have been identified as being associated with cancer. If known mutations are removed, the identified mutations would be new mutations. If a tumor is known to be cancerous, these new mutations could be annotated as being associated with cancer.

II. Mutation Count Filter (MCF)

When sequence reads are aligned to a particular target region, some reads may vary widely from a target region. This may be because several target regions are being analyzed at the same time, because a stray genomic segment was captured by a probe in an enrichment, because a non-cloned genomic segment happened to be sequenced, or for other reasons. As mentioned above, one filter is the mutation count filter (MCF). This filter removes sequence reads that are significantly different than a target When a read is significantly different from the target, it will show many variants. The MCF filter can be used in such situations. A threshold for the total number of variations may be used, or a threshold for the number of a specific type of variation may be used. Both types of thresholds can be used together.

Some embodiments can use this filter with the following parameters for every read with recognized primers: number of substitutions >6, or number of homopolymer indels >5, or number of other simple mutations >5, or total number of simple mutations >10. Other embodiments use the following parameters of: number of substitutions >12, number of homopolymer indels >10, or number of other simple mutations >12, or total number of simple mutations >2.

Figures 2A, 2B:
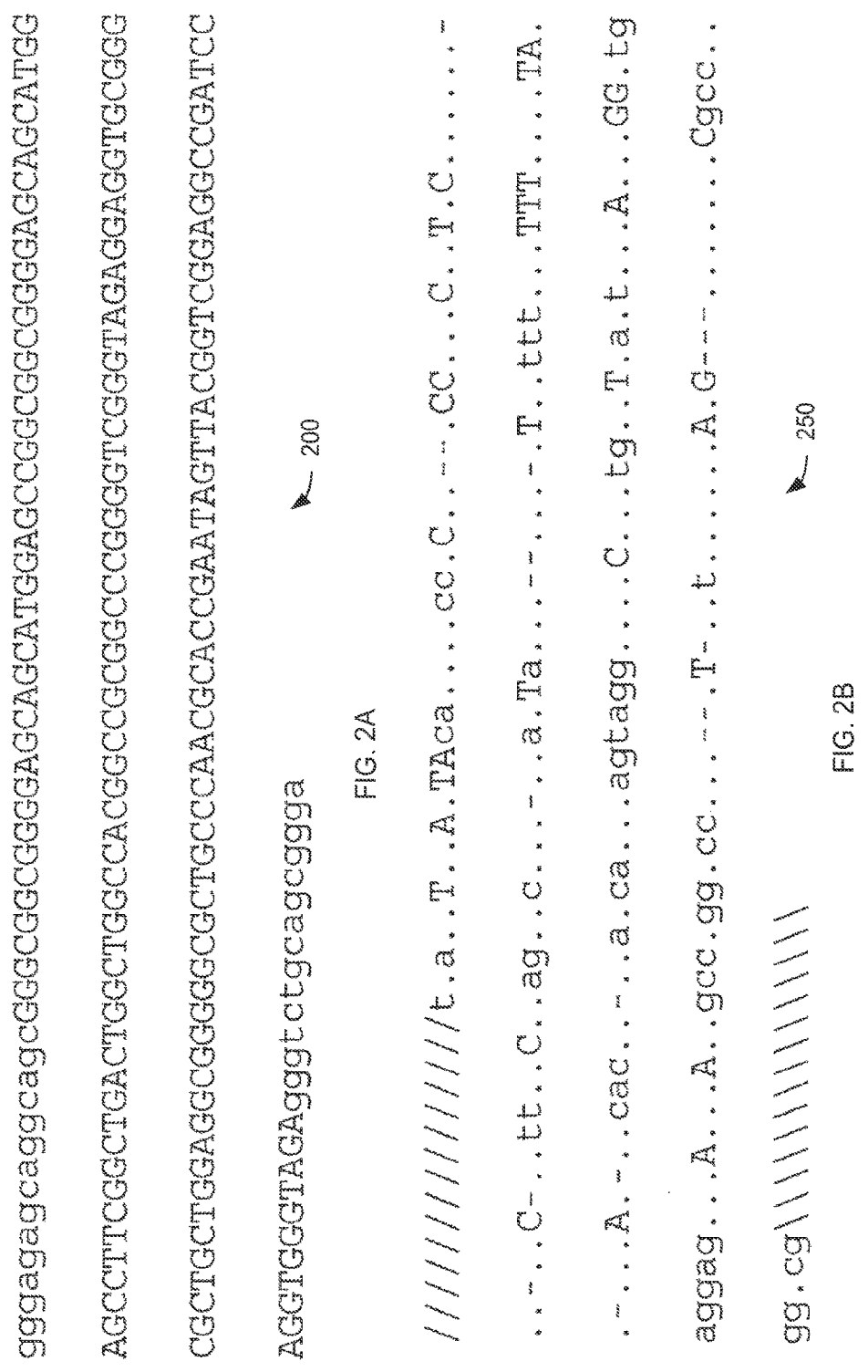

FIG. 2A shows the reference sequence 200 for a target region of the genome. The lower case letters refer to gene-specific primers, and the uppercase letters refer to the genomic target region of interest. In the example shown, the forward primer has 15 bases, and the reverse primer has 15 bases. Specifically, this sequence is from CDKN2A_Exon_1.

FIG. 2B shows a sequence read 250 that was filtered out by MCF according to embodiments of the present invention. In one experiment, there were 325 forward reads and 252 reverse reads having the same pattern of sequence read 250. The symbol "/" denotes the matched base in forward primer, the symbol "\" denotes the matched base in reverse primer, a dot denotes the matched base in target, a dash denotes deletion, a lower case latter denotes insertion base, an upper case letter denotes the substitution base.

As one can see, there are many variations even though the primers match perfectly. Because there are many mutations, these reads are filtered by the MCF and are not used for mutation tally. In one implementation, a mutation tally is a count of the mutations are each position of the target region that appear in the sequence reads determined to correspond to the target region. A tally can include which mutations tend to occur on a same sequence read.

Upon investigation, it was found that sequence read 250 aligns almost perfectly with the cadherin-4 preproprotein on chromosome 20 (note that the gene CDKN2A is on chromosome 9). Thus, these erroneous reads can be attributed to an unintended amplification of a different region of the genome, i.e., other than the target region. The alignment is almost perfect except that there is one additional base at the 5'-end of the query sequence (in the primer region) and four additional bases at the 3'-end of the query sequence. This study indicates that MCF can filter out genomic segments significantly different from the target. It also suggests that development of high fidelity enzyme that can amplify a target region uniquely can be important.

III. Alternate Regions

Given the identification that the primers used for amplification are sometimes not very specific, other regions of the genome can get amplified when the other regions are partly or entirely similar to the target region (e.g., the other region may differ at five locations). Thus, unintended parts of the genome can be amplified during a targeting procedure that occurs before sequencing, as is shown above for FIGS. 2A and 2B. Similarly, enrichment probes for capturing targets may not be very specific.

Such similar sequences could be identified as a mutant read of the target region, but in reality they are simply a wild type sequence from a different part of the genome. These sequences from an alternate part of the genome can therefore result in false positives (i.e. incorrectly be identified as a mutation). The resulting non-target sequence reads can be very different from a target region, and thus mutation count filter (MCF) can be used. However, there may be times where the differences are not great, but the reads are still the result of other parts of the genome being amplified and/or captured. These reads may be quite similar to the target, e.g., having only 3-7 variations. These reads similar to a target region, but not the target, should be excluded from tally of the mutations of the target genes.

FIG. 3 shows a comparison of a sequence read 310 relative to a target sequence (i.e. target region) 320 according to embodiments of the present invention. Sequence read 310 is shown on the top of each of the five rows, and target sequence 320 is shown on the bottom of each of the five rows. The positions of sequence read 310 are shown with labels 311. The top row shows positions 1-60, the second row shows positions 61-120, the third row shows positions 121-180, the fourth row shows positions 181-239, and the fifth row shows positions 240-248, using a 0-based amplicon coordinate system. Positions 1-24 correspond to a forward primer and the last 26 positions correspond to the reverse primer, and the target region is between.

Sequence read 310 was a perfect match in BLAST (Basic Local Alignment Search Tool) to a pseudogene on chromosome 22 and target sequence 320 corresponds to PIK3CA_Exon_10 on chromosome 3. The alignment of sequence read 310 to target sequence 320 using BLAST is shown in the comparison of FIG. 3. Each vertical line between corresponding positions on sequence read 310 and target sequence 320 shows a match, and absence of a vertical line indicates a mismatch. Sequence read 310 is an example of an alternate region for the target region 320.

The alignment shows that there are three variants, one variant 331 is in the primer region at position 6 (transition of C>T) and the other two variants 332 and 333 are in the target region. Variant 332 is at position 174 and shows a transition of A>C. Variant 333 is composed of two differences at positions 198-199 with a transition of GT>C, where T is deleted. In another embodiment, variant 333 can be counted as two separate variations. Variant 331 in the primer region at position 6 shows that a primer can still hybridize when there is a mismatch or that primers can change biochemically and thus hybridize to a different part of the genome. Having only two variations within a relatively long sequence shows that the MCF does not remove all false positives, as true positives can have two variations, and potentially more, up to the cutoff for the MCF.

The existence of these two variants 332 and 333 (an example of mutation combination) would actually correspond to the pseudogene on chromosome 22, instead of being classified as a mutation of PIK3CA_Exon_10 on chromosome 3. Accordingly, if the computer system sees in a sequence read the two variants 332 and 33 that match the pseudogene, then the sequence read should not be counted in a final tally. This same approach can be applied to other alternate regions similar to target region 320, and applied to other target region, as is detailed herein.

Figure 4:
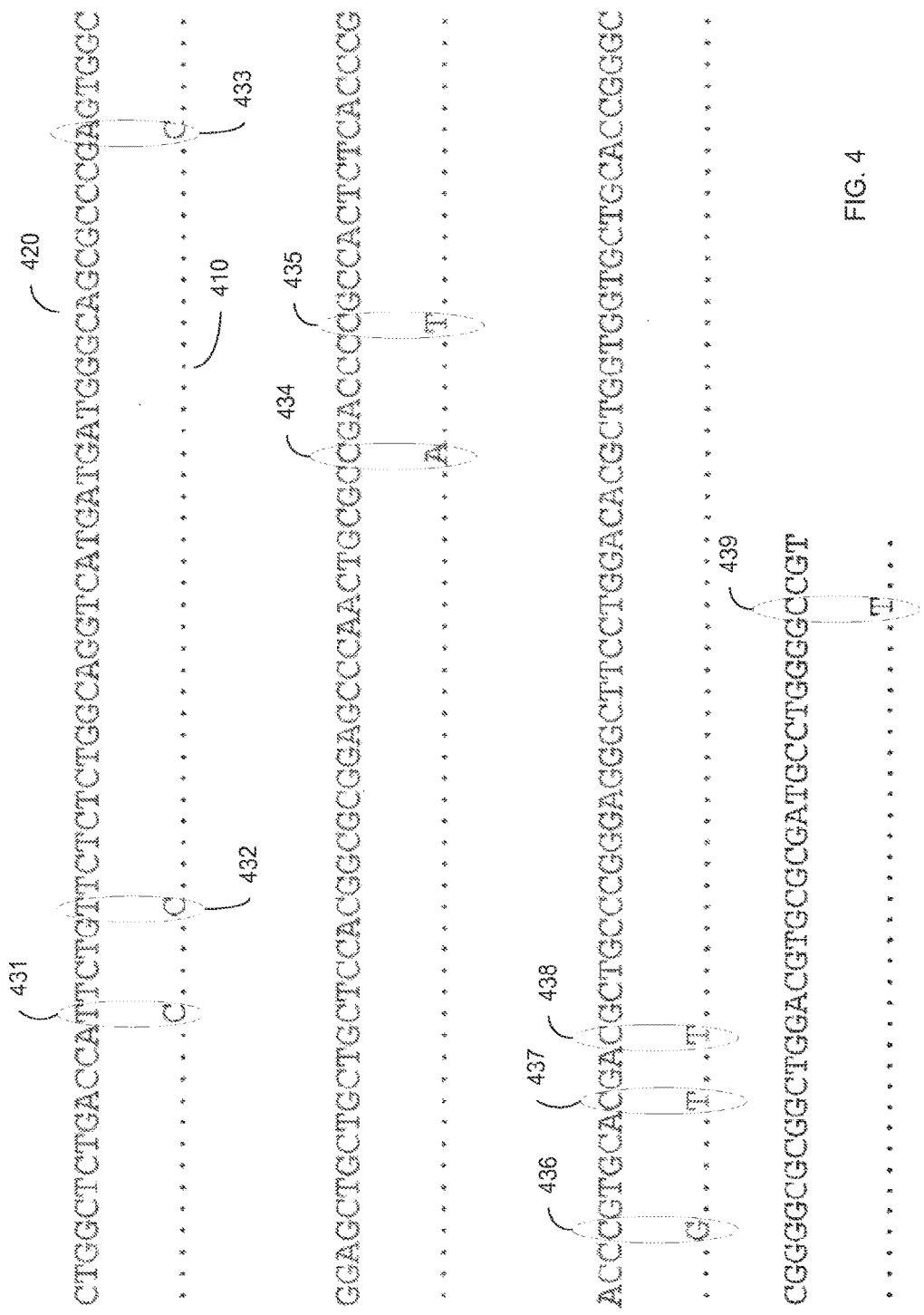
FIG. 4 shows another example of a comparison of a sequence read 410 (SEQ ID NO:6) relative to a target sequence (i.e. target region) 420 (SEQ ID NO:5) according to embodiments of the present invention.

FIG. 4 shows another example of a comparison of a sequence read 410 relative to a target sequence (i.e. target region) 420 according to embodiments of the present invention. Target sequence 420 is shown on the top of each of the three rows, and variants in sequence read 410 are shown on the bottom of each of the three rows. Matches between target sequence 420 and sequence read 410 are shown with a dot "." and the variations are shown as a different base.

Sequence read 410 corresponds to the CDKN2B gene and target sequence 420 corresponds to CDKN2A_Exon_2.1. As one can see, CDKN2B and CDKN2A_Exon_2.1 are similar. Three variants 431, 432, and 439 are in the primer region, with variants 431 and 432 being in the forward primer and variant 439 being in the reverse primer.

There are six mutations (variants) in the target region. Variant 433 is at position 54 showing a transition of A>C. Variant 434 is at position 99 showing a transition of C>A. Variant 435 is at position 105 showing a transition of C>T. Variant 436 is at position 123 showing a transition of C>G. Variant 437 is at position 129 showing a transition of C>T. Variant 438 is at position 123 showing a transition of C>T. This combination of variants can be used to exclude the CDKN2B reads from mutation tally of CDKN2A_Exon_2.1. Given the possibility of mutations in CDKN2B, one embodiment can exclude a sequence reads if it has more than half of the number of variants (in this example, four or more variants) to exclude the sequence read from the tally for CDKN2A_Exon_2.1.

FIG. 5 shows another example of a comparison of a sequence read 510 relative to a target sequence (i.e. target region) 520 according to embodiments of the present invention. Target sequence 520 is shown on the top of each of the three rows, and variants in sequence read 510 are shown on the bottom of each of the three rows. Matches between target sequence 520 and sequence read 510 are shown with a dot "." and the variations are shown as a different base.

Target sequence 520 corresponds to PTEN_Exon_5.1.2 and sequence read 410 corresponds to a similar genomic segment (i.e. an alternate region). One variant 531 is in the primer region, and the three variants 532-534 are in the target region. Variant 532 shows a transition of G>A. Variant 533 shows a transition of A>T. Variant 534 shows a transition of G>A. Again, this combination of variants in the target region can be used exclude those reads from a mutation tally of PTEN_Exon_5.1.2. Various methods can be used to identify alternate regions, e.g., using embodiments described herein.

IV. Differentiating Between Target and Alternate Regions

As shown above, some parts of a genome (e.g., a human genome) can be similar to other parts of the genome. As a result, a sequence read obtained from a targeted sequencing process (e.g., amplification or enrichment following by a sequencing using universal adapters) might be similar to a target region, but in fact be from another part of the genome. For example, an amplification primer pair might amplify more than one part of the genome. Good primer design can reduce or sometimes avoid such unintended amplification, but this is not always possible.

To identify that a genomic segment is actually from a non-target region, algorithms can align the sequence reads to the whole genome to find the best match. However, aligning a sequence to the whole genome can be quite expensive in terms of computational time. In particular, mapping large amount of reads to the whole human genome is challenging in terms of computational time and resource.

To accelerate the mapping process with little or no loss of information about alternative regions, some embodiments can: (1) identify the alternative sequence segments similar to the reference genes of interest, (2) map the reads to the reference genes of interest, (3) map the reads to the alternative segments, and (4) find the best mapping obtained from (1) and (3). A read might align to several of the regions tested. In this case, the quality (e.g., number of mismatches) of the alignment can be used to determine the best match.

Embodiments can increase the computational speed and reduce the computer memory requirements. Embodiments can also take advantage of parallel computing to make computation even faster. Embodiments are not limited to sequencing. For example, since PCR and enrichment results may also be analyzed with sequencing, embodiments can be used to identify potential causes of false positives in PCR tests and enrichment-based tests.

Figure 6:
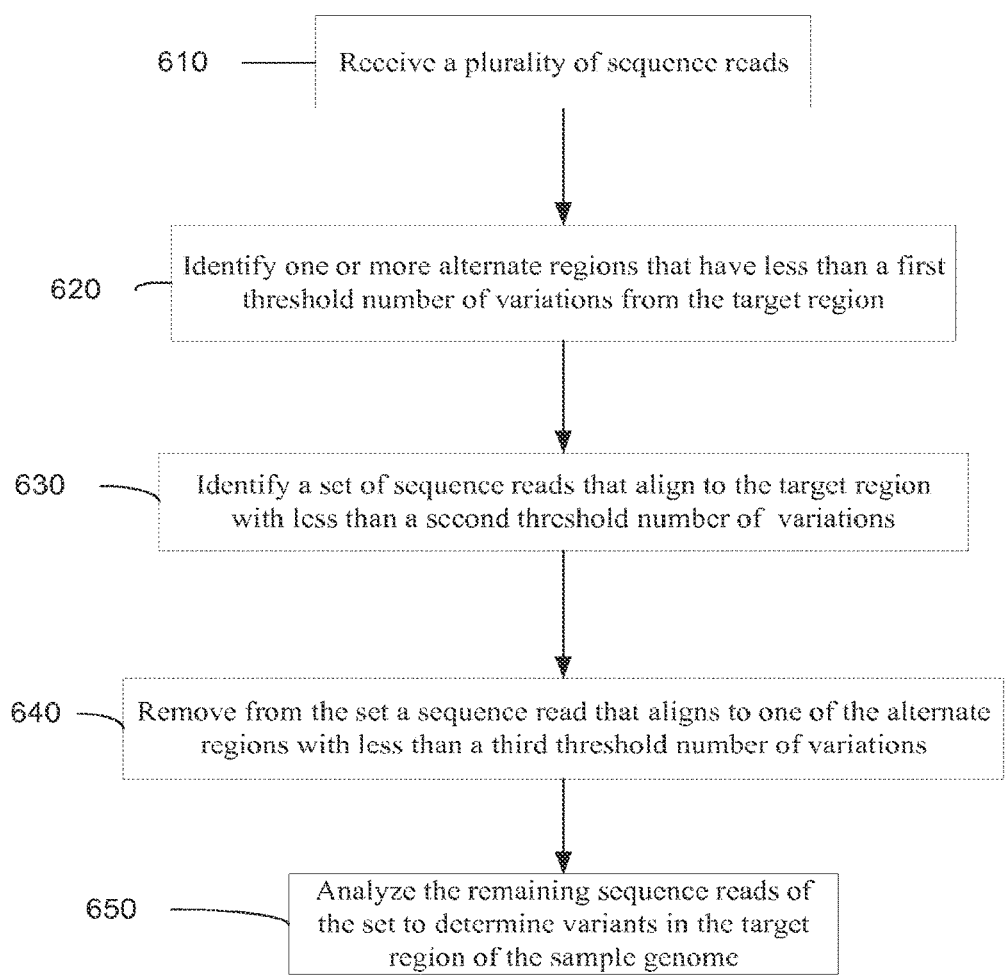
FIG. 6 is a flowchart illustrating a method of detecting variants in a target region of a sample genome of an organism according to embodiments of the present invention.

FIG. 6 is a flowchart illustrating a method of detecting variants in a target region of a sample genome of an organism according to embodiments of the present invention. Method 600 can be used as part of a process that is used to detect variants that might be related to cancer. Alternate regions can be identified in a previously performed process or identified as part of a same process (e.g., using the same sequencing results) used to detect the variants.

At block 610, a plurality of sequence reads are received. The sequence reads are obtained from sequencing a plurality of genomic segments in a sample obtained from the organism (e.g. a human or animal). The sequencing includes targeting genomic segments from the target region. For example, an amplification or enrichment step can be performed to increase the percentage of genomic segments from one or more target regions in the sample. Then, when sequencing is performed, the likelihood of sequencing (e.g., using universal adapters) a genomic segment from a target region is increased. In one embodiment, about 3,000 sequence reads per sample are received. Other embodiments can receive more or less.

At block 620, one or more alternate regions that have a respective first number of variations from the target region of a reference genome are identified. Each respective first number is greater than one and less than a first threshold number. For example, a first region might have 5 variations from the target region in a reference genome. If the first threshold number is greater than 5, then the first region can be identified as a first alternate region.

If there is more than one alternate region, the different alternate regions can have different numbers of variations relative to the target region, and thus the respective first numbers can be different. Examples of the first threshold number are a value between 6 and 10, including real numbers (i.e. not just integers). The alternation regions can include known mutations, and even regions from other genomes well. For example, an alternate region can correspond to a viral genome or other embedded sequences.

In one embodiment, the alternate regions can be identified by accessing a database that stores previously identified alternate regions for corresponding target regions. For instance, a target region can have a corresponding identifier, and that identifier can be used to cross-reference the one or more alternate regions that correspond to the target region. Thus, after a user enters a particular target region into the software, the software can retrieve from memory the alternate regions to be used in analyzing the results of the current sequencing run. In another embodiment, the alternate regions can be identified using data from the present sequencing run.

At block 630, a set of sequence reads that align to the target region of the reference genome with less than a second threshold number of variations is identified. The plurality of sequence reads can be aligned to the target region of the reference genome via any suitable process, e.g., using BLAST. The number of variations can be counted as the number of positions where a base is different. In other embodiments, neighboring positions (contiguous are simply with a specific number of positions) where a difference exists can be treated as a single variation.

The second threshold number can have any value. In one embodiment, the second threshold number is one half the first threshold number plus one. For example, if the first threshold number is 10, then the second threshold number can be chosen as six. A reason for such a choice is explained below. The second threshold number can be the same or greater than the first threshold number, but for reasons described herein, smaller values can provide more efficient results.

A sample can be tested for more than one target region at a time. Thus, the alignment can be made to each of the target regions. But, if the targets are already identified and retrieved from memory, the alignment need only be made to the target regions being investigate. Thus, if the sample is being investigated for a first target region and a second target region, then the sequence reads may be aligned only to the first target region and the second target region.

At block 640, a sequence read that aligns to one of the alternate regions with a second number of variations that is less a third threshold number can be removed from the set. In one embodiment, the third threshold number is one half of the corresponding first number of variations is removed from the set. For example, assume a first alternate region has six variations relative to the target region. Then, the corresponding first number of variations is six. If a first sequence read has two variations relative to the first alternate region (and potentially four variations from the target region), then the first sequence read would be removed. As first sequence read is more similar to the first alternate region, it can be estimated that the first sequence read is a result of a mutation of the alternate region and not a mutation of the target region. All of such sequence reads that align better to an alternate region would typically be removed, but certain criteria could be used as an exception to keep some of such sequence reads.

In other embodiments, more stringent or less stringent third threshold number can be used, i.e., less than or greater than one half of the corresponding first number of variations. For example, the third threshold number could be equal to one (no variations). However, if the alternate region was determined from a different patient and retrieved from memory, then it is possible that a mutation of the alternate region in the present sample could contribute reads to the set. To address such an issue, the sequence reads could be marked to indicate a level that a sequence read aligns to an alternate region. For example, a sequence read that has one or two variations from an alternate threshold could be kept, but marked as being similar to an alternate region. If the first number of variations of the alternate region were large enough (e.g., 10) other classifications of the level of difference of a sequence read could be larger numbers (such as 3 or 4).

The alignment of a sequence read to an alternate region can be performed using a same or similar process as the alignment to the target region. For example, BLAST can be used. In another embodiment, the alignment of the a sequence read to an alternate region can be accomplished using knowledge of the variations between the target region and the alternate region and the alignment to the target region. For example, if the target region and the alternate region are known to have five specific variations (e.g., the base differences at specific locations), an alignment of a sequence read to the target region that shows four of the five specific variations would provide an alignment to the alternate region with the fifth specific variation. This can provide a quicker alignment that directly using a raw alignment procedure that does not use knowledge of the variations between the target region and the alternate region.

At block 650, the remaining sequence reads of the set can be analyzed determine variants in the target region of the sample genome. For example, the variations of the remaining sequences can be counted. In one embodiment, each variation at a particular position is counted. If the variation occurs a sufficient number of times (e.g., as compared to an absolute number or compared to a percentage of the total reads in the set), then then variation can be classified as a mutation. The efficiency and sensitivity of coverage of embodiments can be assessed by comparison with the computationally intensive techniques that map to the whole genome to identify a best match.

V. Identifying Alternate Regions

The identification of one or more alternate regions that have less than the first threshold number of variations relative to a target region can be performed in a variety of ways. One method is to search the whole database to find similar sequences. But, this approach is time consuming and can lack the information how the similar sequences will be amplified in experiments.

Another approach is to make use of complex mutations (e.g., mutation combinations) that occur on the same sequence reads. A report can be generated to that shows the joint frequencies of combinations of two or more simple mutations. Mutation combinations that occur a sufficient amount (e.g., at least 1%) is an indication that the mutation is really the existence of an alternate region. Such alternative genomic segments may also be from a common mutation of the target region. For example, a common mutation may occur between different populations, where the segment of one population can be viewed as an alternate of the segment for a different population (e.g., European vs. Asian ancestry).

In one implementation, for a combination of simple mutations to be an alternative genomic segment that has significant influence on mutation tally, certain conditions can be used. Example conditions are as follows. The combination mutation should appear in multiple samples and multiple runs of the training dataset. Second, the frequency of the combination mutation within a sample should not be negligible (e.g., greater than 1%). Third, the corresponding sequence should have nearly perfect match (e.g., only one or two mismatches) with a genomic segment that is different from the target.

Figure 7:
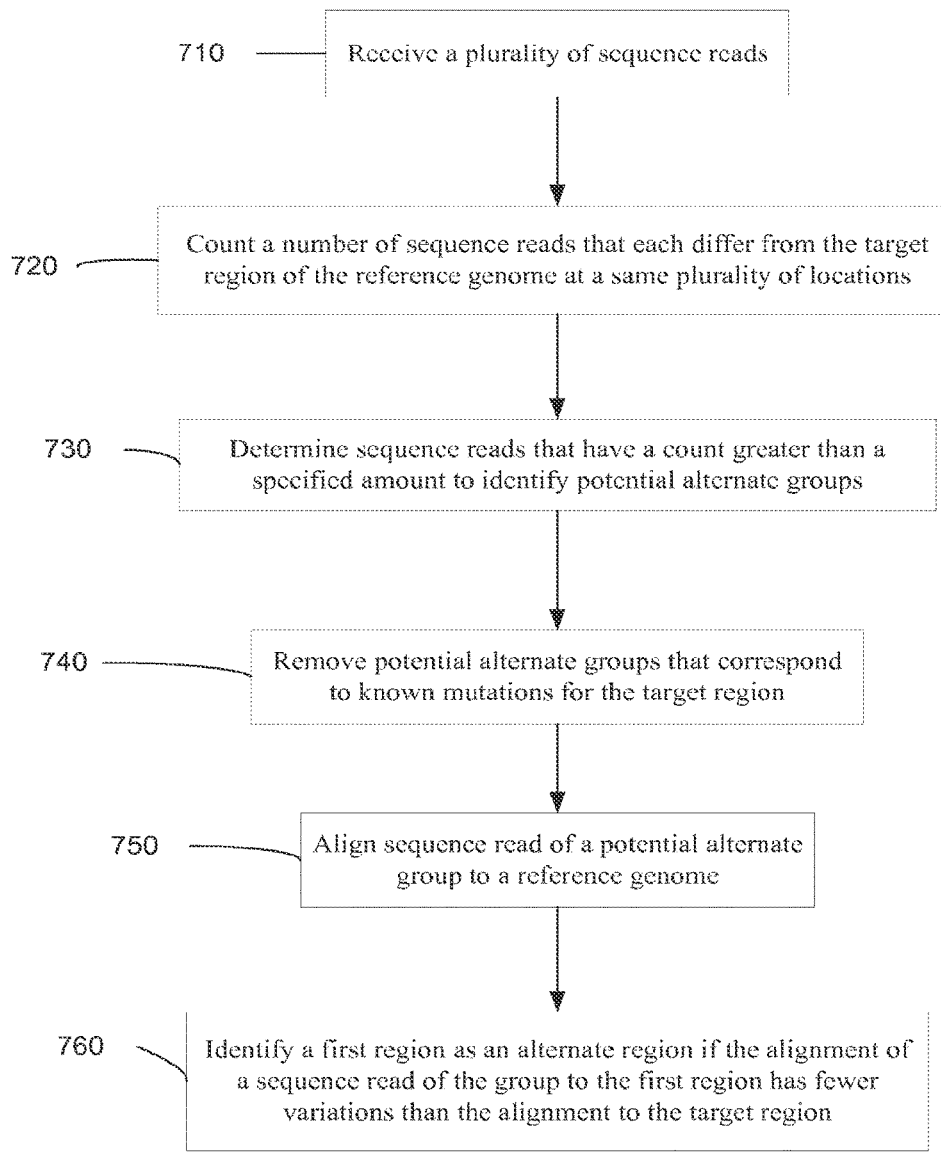
FIG. 7 is a flow chart of a method 700 for identifying an alternate region corresponding to a target region according to embodiments of the present invention.

FIG. 7 is a flow chart of a method 700 for identifying an alternate region corresponding to a target region according to embodiments of the present invention. Method 700 can be performed as an initial process on one or more investigatory samples and the identified alternate region(s) that correspond to particular target regions can be stored or provided in software to end users (e.g., labs). In this manner, the end users do not have to identify the alternate regions themselves. Thus, after a user enters particular target regions into the software, the software can retrieve from memory these previously identified alternate regions to be used in analyzing the results of the current sequencing run.

At block 710, a plurality of sequencing reads are obtained. The sequencing process involves targeting one or more target regions, as described herein. In one embodiment, method 700 can be performed using sequencing results from an initial sequencing run that is performed before the test sequencing run that is used to identify mutations. This initial sequencing run can use an investigatory sample that differs from the sample being tested for mutations. The investigatory sample could be from the same organism or from a different organism. This initial sequencing run can obtain a similar amount of reads (e.g., 2,000 to 3,000). Such an initial sequencing run can be used to identify alternate regions, which can be used for futures test runs for other patients. In another embodiment, at least a portion of the same sequence reads used to identify mutations can be used to identify the alternate regions. Thus, the same sequencing run may be used.

At block 720, a number of sequence reads that each differ from the target region of the reference genome at a same plurality of locations are counted. The sequence reads that have the same variations relative to the target region can be placed into a same alternate group, as they may related to a same alternate region. As the variations are the same, these reads may be suggestive of an alternative region in the genome. For example, 100 sequence reads could differ from a target region by the exact same 6 variations. These 100 sequence reads can be identified and the count of 100 stored and tracked.

The sequence reads can be identical with a contiguous region, e.g., the region that is compared to the target region. But, in some embodiments, the sequence reads do not have to be identical within such a contiguous region. For instance, the sequence reads could vary at some middle region. Such differences in the sequences of an alternate could be required to be below a specific number that is an absolute value or that is set as a percentage. For example, the sequence reads of the alternate group could be required to share at least X % of these variations (e.g., 70%, 80%, or 90%). Such differences within an alternate group can result from heterozygous mutations, where two genomic segments are from the same alternate region but are from different chromosomes.

In one implementation, sequence reads can be clustered when differences among the sequence reads of an alternate group are allowed. The coordinates can be the base value at each position. A centroid of the cluster could be identified (e.g., most common sequenced) and sequences that differ by a specific number of bases could be included.

In one embodiment, the number of shared variations of an alternate group can be capped at a specified value. For example, reads that differ from the target region by more than a threshold number (e.g., the first threshold from method 600) of variations could be removed from consideration of adding to an alternate group. This threshold could be the same as used for an MCF procedure. Since such reads would be removed in the normal run, there may not be much purpose in determining an alternate region whose reads would not be counted.

In one implementation, the threshold for considering a sequence read for adding to an alternate group can be more than an MCF threshold. For example, such an alternate region (i.e. more variations than MCF) might be useful, as some sequence reads could be below the MCF but more similar to the alternate region (e.g., MCF of 10 with a first threshold of 14 for an alternate region could have a sequence read with 8 being more similar to the alternate region). Thus, this threshold could be twice as much as for MCF. In another implementation, the threshold for considering a sequence read for adding to an alternate group could be larger than a final threshold requirement for the number of variations in an alternate region. For example, if the sequence reads of an alternate region do not have to be identical, some sequence reads could have more than the threshold for the number of shared variations allowed.

At block 730, sequence reads (e.g., of an alternate group) that have a count greater than a specified amount (a cutoff value) are determined. This specific amount can also be considered an abundance filter. For example, the specified amount could be an absolute number (such as 200 or 300), or a percentage of the total reads (e.g., 1%). In one aspect, an assumption is that such a small count would not occur if the mutation combination was from an actual part of the genome.

The output is a plurality of alternate groups of variations that are determined to occur together. In this way, if only a few such reads have this mutation, then the variations are likely an artifact, and not related to a real part of the genome. Also, such reads would not survive an abundance filter to identify mutations, and thus no benefit may be obtained.

At block 740, alternate groups that correspond to known mutations for the target region can be removed. This step is optional, as can be other steps of other methods. A database could searched for mutations that are medical meaningful or for mutations that are known to occur, but are not related to disease. For the latter, such known mutations can occur in a significant portion of a population. The reference could be chosen from the same population as the sample, or the known mutations can simply include the known mutations of that population. If the sequencing data is for an actual test sample, this correspondence to a known mutation can result in calling the mutation for the sample.

At block 750, a sequence read of a remaining alternate group (i.e., whose number exceeds the specified amount) can be an aligned to a reference genome. Any points of variation among the reads of an alternate group can independently be aligned (e.g., two alignments for each allele of a SNP). For example, two sub-clusters could be identified for a cluster of similar sequences (e.g., differing by a SNP or other polymorphism), and both sub-clusters could be aligned.

At block 760, if the alignment of a read of a group to a first region has fewer variations than the alignment to the target region, the first region can be identified as an alternate region. Thus, the alignment can provide the best matching region. If there is another region that provides a better match (or potentially the same) as the target region, then that region can be identified as an alternate region. These alternative regions can then be stored in memory, and then accessed for use when the target region is used in a future run. For example, a user might enter the target regions into a computer, which can then search a database to identify alternate regions.

In one embodiment, if no alternate region is found (i.e. no other region is a better match), then the variations can be identified as mutations of the target region. Such a mutation could be stored in a database of known mutations, and used in methods above.

As an example, an alignment of reads from a sequencing run showed a new mutation in EGFR exon 19 at positions 2237-2248. The mutation was AATTAAGAGAAG>CCC (SEQ ID NOS:9 and 10). It was noticed that a substitution at position 2250 (A>G) appeared in similar frequency, which suggest the mutations were a combination mutation and occurred jointly. It was confirmed the mutations occurs on the same reads. Thus, the mutation should be described for positions 2237-2250 as AATTAAGAGAAGCA>CCCCG (SEQ ID NOS:11 and 12), which is a combination of two simple mutations. A complex mutation report is better than simply identifying that two or more simple mutations have similar frequencies because they may not appear in the same reads and the joint frequency may be low. Moreover, it is possible that a subset of the combination may appear in higher joint frequency and make the frequencies of whole combination uneven.

Accordingly, an embodiment of using a report on complex mutations can efficiently find alternative genomic segments with two or more simple variants from the target. It is also possible that an alternative genomic segment contains 0 or 1 variant from the target. In one embodiment, in design of primers, effort was used to eliminate identical segment from different genomic locations. If the difference is only one simple variant, a report about single simple variants can be used with embodiments described above to identify and remove the false positive reads with one simple variant difference from the target.

The table in FIG. 9 shows complex mutations (combinations of simple mutations) that appear in multiple samples and multiple runs. The complex mutations correspond to the examples of FIGS. 3-5. A database search justified that they correspond to the alternative human genomic segments. As mentioned before, this search can be extended to other organisms such as viruses.

For enrichment, identification of alternate sequence segments similar to the target region can proceed as follows. Depending on different purposes, for a target gene of interest, some embodiments can either include the target exons with adjacent splicing sites, or include promoter, 5'-UTR, 3'-UTR, introns and exons. The target sequence can be divided into small overlapping segments, for example, a segment can be 150-base long, and two overlapping segments can have 75-base overlap). These segments can be treated as reads and mapped to the whole genome to find alternative segments with high similarity. These alternative segments can be included in one or multiple files. New annotations can be made, and new reference sequence coordinates can be associated with the original genome coordinates, e.g., as part of identifying an alternate region for a target region.

VI. Computer System

Figure 8:
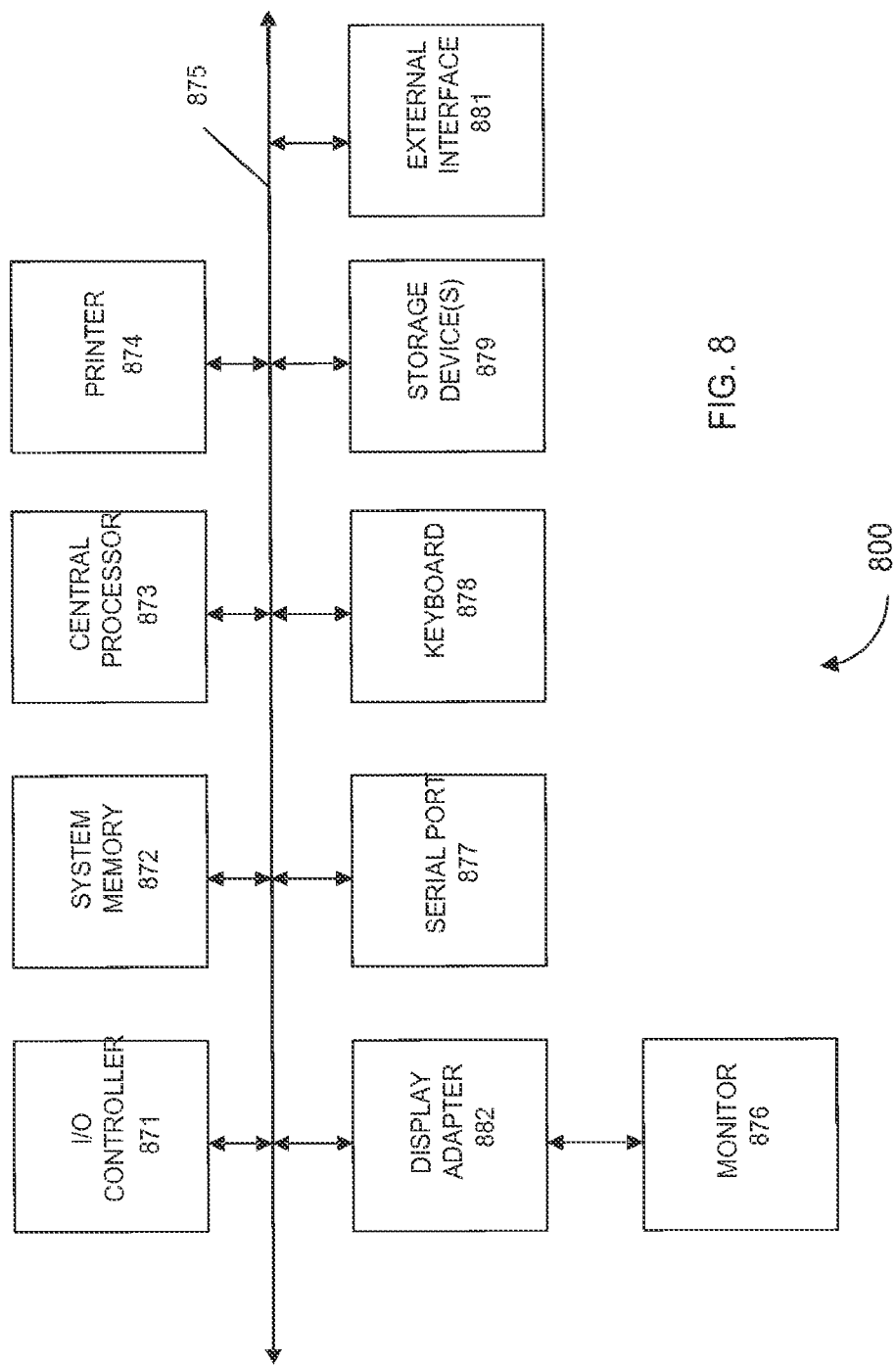
FIG. 8 shows a block diagram of an example computer system 800 usable with system and methods according to embodiments of the present invention.

Any of the computer systems mentioned herein may utilize any suitable number of subsystems. Examples of such subsystems are shown in FIG. 8 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk), as well as the exchange of information between subsystems. The system memory 872 and/or the storage device(s) 879 may embody a computer readable medium. Any of the values mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of identifying an alternate region associated with a target region in a reference genome using a sample of an organism, the method comprising:
   receiving, with a computer system, a plurality of sequence reads, the sequence reads obtained from sequencing genomic segments in one or more samples including the sample obtained from the organism, wherein the sequencing includes targeting genomic segments from the target region;
   performing, by the computer system, an alignment of the plurality of sequence reads to the target region in the reference genome to identify a set of sequence reads that align to the target region of the reference genome with less than a threshold number of variations;
   counting, by the computer system, a first number of sequence reads of the set of sequence reads that share a set of variations from the target region in the reference genome, the first number of sequence reads forming an alternate group;
   if the first number exceeds a cutoff value, performing, by the computer system, an alignment of a first sequence read from the alternate group to the reference genome; and
   if the alignment of the first sequence read to a first region in the reference genome has fewer variations than the alignment to the target region, identifying the first region as an alternate region,
   wherein the alternate region is used to exclude, from sequence reads of a test sample for determining one or more variants in the target region in the test sample, one or more sequence reads that align to the alternate region with fewer variations than to the target region.

2. The method of claim 1, wherein the sequence reads of the alternate group are identical within a contiguous region.

3. The method of claim 1, further comprising:
   comparing the first sequence read to a database of known mutations of the target region; and
   if the first sequence read corresponds to a known mutation of the target region, discarding the alternate group as corresponding to an alternate region.

4. The method of claim 1, wherein targeting genomic segments from the target region includes amplifying genomic segments using a pair of primers that are designed to amplify the target region.

5. The method of claim 1, wherein targeting genomic segments from the target region includes using probes anchored to a surface to select genomic segments from the target region.

6. The method of claim 1, further comprising:
   storing the alternate region and associated target region in a database.

7. The method of claim 6, wherein the target region has a corresponding identifier in the database for cross-referencing one or more alternate regions associated with the target region.

8. The method of claim 1, wherein the cutoff value is 1%.

9. The method of claim 1, further comprising:
   analyzing sequence reads that align to the target region in the reference genome with fewer variations than the alignment to the first region to determine one or more variants in the target region in a sample genome.

10. The method of claim 9, wherein the reference genome includes a different genome of another organism different from the organism, and wherein the first region is from the different genome.

11. The method of claim 9, wherein the sample of the organism is an investigatory sample that is used to identify the first region as an alternate region, and wherein the investigatory sample is different from the test sample from which the sequence reads are analyzed to determine the one or more variants of the sample genome of the test sample.

12. The method of claim 11, further comprising:
amplifying the genomic segments from the target region in the investigatory sample;
sequencing the genomic segments from the target region in the investigatory sample to obtain the plurality of sequence reads;
amplifying genomic segments from the target region in the test sample; and
sequencing the genomic segments from the target region in the test sample to obtain the sequence reads of the test sample.

13. The method of claim 9, wherein the sample genome is of the sample of the organism.

14. The method of claim 1, wherein the sequence reads in the alternate group each differ from the target region in the reference genome only at a same plurality of locations.

15. The method of claim 1, further comprising:
excluding, from the alternate group, sequence reads that differ from each other by more than a threshold number of locations.

16. The method of claim 15, wherein excluding sequence reads from the alternate group includes:
identifying a centroid of a cluster of sequence reads; and
excluding sequence reads that differ from the centroid by more than the threshold number of locations.

17. The method of claim 1, wherein the sequencing is performed in a run that sequences two or more samples, wherein the genomic segments include an identification (ID) that corresponds to one sample of a plurality of samples, and wherein at least two samples have a different target region.

18. A computer product comprising a non-transitory computer readable medium storing a plurality of instructions that when executed control a computer system to identify an alternate region associated with a target region in a reference genome using a sample of an organism, the instructions comprising:
receiving, by the computer system, a plurality of sequence reads, the sequence reads obtained from sequencing genomic segments in one or more samples including the sample obtained from the organism, wherein the sequencing includes targeting genomic segments from the target region;
performing, by the computer system, an alignment of the plurality of sequence reads to the target region in the reference genome to identify a set of sequence reads that align to the target region of the reference genome with less than a threshold number of variations;
counting, by the computer system, a first number of sequence reads of the set of sequence reads that share a set of variations from the target region in the reference genome, the first number of sequence reads forming an alternate group;
if the first number exceeds a cutoff value, performing, by the computer system, an alignment of a first sequence read from the alternate group to the reference genome; and
if the alignment of the first sequence read to a first region in the reference genome has fewer variations than the alignment to the target region, identifying the first region as an alternate region,
wherein the alternate region is used to exclude, from sequence reads of a test sample for determining one or more variants in the target region in the test sample, one or more sequence reads that align to the alternate region with fewer variations than to the target region.

19. The computer product of claim 18, wherein the instructions further comprise:
analyzing sequence reads that align to the target region in the reference genome with fewer variations than the alignment to the first region to determine one or more variants in the target region in the sample genome.

20. A system for identifying an alternate region associated with a target region in a reference genome using a sample of an organism, the system comprising:
one or more processors configured to:
receive a plurality of sequence reads, the sequence reads obtained from sequencing genomic segments in one or more samples including the sample obtained from the organism, wherein the sequencing includes targeting genomic segments from the target region;
perform an alignment of the plurality of sequence reads to the target region in the reference genome to identify a set of sequence reads that align to the target region of the reference genome with less than a threshold number of variations;
count a first number of sequence reads of the set of sequence reads that share a set of variations from the target region in the reference genome, the first number of sequence reads forming an alternate group;
if the first number exceeds a cutoff value, perform an alignment of a first sequence read from the alternate group to the reference genome; and
if the alignment of the first sequence read to a first region in the reference genome has fewer variations than the alignment to the target region, identify the first region as an alternate region,
wherein the alternate region is used to exclude, from sequence reads of a test sample for determining one or more variants in the target region in the test sample, one or more sequence reads that align to the alternate region with fewer variations than to the target region.

21. The system of claim 20, wherein the one or more processors are further configured to:
compare the first sequence read to a database of known mutations of the target region; and
if the first sequence read corresponds to a known mutation of the target region, discard the alternate group as corresponding to an alternate region.

* * * * *